United States Patent [19]

Schield et al.

[11] Patent Number: 5,160,642
[45] Date of Patent: Nov. 3, 1992

[54] POLYIMIDE QUATERNARY SALTS AS CLAY STABILIZATION AGENTS

[75] Inventors: John A. Schield, Chesterfield; Michael I. Naiman; Gary A. Scherubel, both of St. Louis, all of Mo.

[73] Assignee: Petrolite Corporation, St. Louis, Mo.

[21] Appl. No.: 529,026

[22] Filed: May 25, 1990

[51] Int. Cl.$^5$ ............... E21B 43/26; C07D 207/452; C08F 26/02
[52] U.S. Cl. ............... 252/8.551; 526/262; 525/66; 548/521; 548/522
[58] Field of Search ............... 526/262; 525/66; 252/8.551; 548/521, 522

[56] References Cited

U.S. PATENT DOCUMENTS

| | | |
|---|---|---|
| 3,291,679 | 12/1966 | O'Brien ............... 526/262 X |
| 3,778,416 | 12/1973 | Zoller et al. ............... 8/181 X |
| 4,366,071 | 12/1982 | McLaughlin et al. ............... 252/8.551 |
| 4,366,072 | 12/1982 | McLaughlin et al. ............... 252/8.551 |
| 4,366,073 | 12/1982 | McLaughlin et al. ............... 252/8.551 |
| 4,366,074 | 12/1982 | McLaughlin et al. ............... 252/8.551 |
| 4,374,739 | 2/1983 | McLaughlin et al. ............... 252/8.551 |
| 4,434,076 | 2/1984 | Mardis et al. ............... 252/8.551 X |
| 4,440,649 | 4/1984 | Loftin et al. ............... 252/8.551 X |
| 4,460,483 | 7/1984 | Weaver ............... 252/8.551 |
| 4,497,596 | 2/1985 | Borchardt et al. ............... 252/8.551 X |
| 4,505,833 | 3/1985 | Lipowski et al. ............... 252/8.551 X |
| 4,536,303 | 8/1985 | Borchardt ............... 252/8.551 |
| 4,536,304 | 8/1985 | Borchardt ............... 252/8.551 |
| 4,536,305 | 8/1985 | Borchardt et al. ............... 252/8.551 |
| 4,563,292 | 1/1986 | Borchardt ............... 252/8.551 |
| 4,626,363 | 12/1986 | Gleason et al. ............... 252/8.551 X |
| 4,627,926 | 12/1986 | Peiffer et al. ............... 252/8.551 |
| 4,652,621 | 3/1987 | Kadono et al. ............... 252/8.551 X |
| 4,693,639 | 9/1987 | Hollenbeak et al. ............... 252/8.551 X |
| 4,828,726 | 5/1989 | Himes et al. ............... 252/8.551 X |
| 4,842,073 | 6/1989 | Himes et al. ............... 252/8.551 X |
| 4,959,163 | 9/1990 | Holtmyer et al. ............... 252/8.551 |

FOREIGN PATENT DOCUMENTS

WO88/04680 6/1988 PCT Int'l Appl. .

Primary Examiner—Robert L. Stoll
Assistant Examiner—Gary L. Geist
Attorney, Agent, or Firm—Jeffrey S. Boone; Kenneth Solomon

[57] ABSTRACT

A clayish formation, such as encountered in rock surrounding an oil well bore, is stabilized with a quaternary ammonium salt of an imide of polymaleic anhydride. The invention is particularly relevant to hydraulic fracturing fluids used for enhanced oil recovery.

22 Claims, No Drawings

POLYIMIDE QUATERNARY SALTS AS CLAY STABILIZATION AGENTS

BACKGROUND OF THE INVENTION

This invention relates to the stabilization of clay formations, particularly those encountered in the drilling of and production from oil wells. More particularly, this invention is concerned with such stabilization by means of chemical agents.

Production of petroleum hydrocarbons is often troubled by the presence of clays and other fines capable of migrating in the formation. Normally, these fines, including the clays, are quiescent, causing no obstruction of flow to the well bore via the capillary system of the formation. However, when the fines are disturbed, they begin to migrate in the production stream and, too frequently, they encounter a constriction in the capillary where they bridge off and severely diminish the flow rate.

The agent that disturbs the quiescent fines is frequently the introduction of a water foreign to the formation. The foreign water is often fresh or relatively fresh water compared to the native formation brine. The water is frequently intentionally introduced for purposes of hydraulic fracturing of the formation rock to increase production rates. In any event, the change in the water can cause fines to disperse from their repository or come loose from adhesion to capillary walls.

Sometimes the loss of permeability is due to clay swelling with relatively fresh water without migration. But, often clay swelling is accompanied by migration of fines. Sometimes non-swelling clays can respond to the foreign water and begin to migrate. It is believed that swelling clays are the major mechanism of fines migration and/or swelling, because when formation cores are analyzed, the presence of swelling clays are an excellent indicator that the formation will be sensitive to foreign water intrusion, while the presence of non-swelling clays only is inconclusive.

Generally, swelling clays are in the smectic group including clay minerals such as montmorillonite, beidellite, nontronite, saponite, hectorite, and sauconite. Of these, montmorillonite is the clay mineral found most commonly in formation core analysis. Montmorillonite is commonly associated with clay minerals known as mixed-layer clays. Further information is contained in *Jackson's Textbook of Lithology*, pages 95 to 103.

Migrating fines including a host of clay and other minerals in minute particle size, for example, feldspars, fine silica, allophane, biotite, talc, illite, chlorite and the swelling clays themselves. Further information is contained in Theng's *The Chemistry of Clay-Organic Reactions*, pages 1 to 16.

Clays can also cause trouble in areas other than permeability reduction. When they are a component in shales, sandstones, or other formations, contact with a foreign water or at times with any water can cause the formation to lose strength or even disintegrate. This is a problem in building foundations, road beds, drilling wells, and any situation where the formation strength is important.

There have been numerous attempts to control the ill effects of water on clay and/or other fines. These have been principally in the oil industry. One idea is to convert the clay from the swelling sodium form or the more rare swelling lithium form to another cation form which does not swell as much.

Example cations that form relatively non-swelling clays are potassium, calcium, ammonium and hydrogen ions. When a solution of these cations, mixed or individually, flows past a clay mineral, they readily replace the sodium ion and the clay is transformed to a relatively non-swelling form (refer to Theng, Tables 2, 3, and 4). The use of acid, potassium, calcium, or ammonium ions to exchange for sodium ion has been successful in preventing damage to formations susceptible to plugging or disintegrating due to clays in their compositions.

One specific approach is that of U.S. Pat. No. 4,366,074 (McLaughlin - Halliburton, 1982) which teaches the use of a very wide variety of polymers, including poly(acrylamide-3-propyltrimethylammonium chloride):

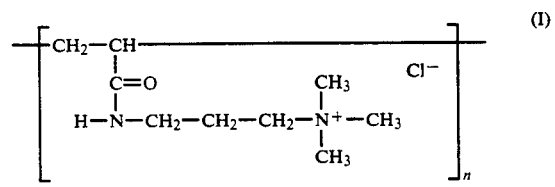

as clay stabilizers. While the illustrated compound is effective in shallow wells, it decomposes and loses its effectiveness at the higher temperatures encountered in deep wells.

WO 88/04680 (Meunier - Elf, 1988) teaches the use of quaternary salts of copolymers of an unsaturated acid or anhydride (including maleic anhydride) and another unsaturated compound (hydrocarbon, ester, or either), in a ratio of 1:1 to 1:4. While these materials are operable, they do not provide as high a degree of stabilization as is desired.

Accordingly, it would be desirable to provide a clay stabilization composition that would provide a high degree of stabilization and that would not decompose at the temperatures encountered in deep oil wells.

SUMMARY OF THE INVENTION

In one aspect, the invention is a quaternary salt of a homopolymer of maleic anhydride which has been reacted with an alkyl diamine.

In another respect, the invention is a method of stabilizing clay formations by contacting the formation with the above compound.

DETAILED DESCRIPTION OF THE INVENTION

In this specification and claims, numerical values are not critical unless otherwise stated. That is, the numerical values may be read as if they were prefaced with the word "about" or "substantially".

A first component useful in the invention is maleic anhydride:

Maleic anhydride is well known to those skilled in the art and is commercially available.

The maleic anhydride is polymerized to form a homopolymer. By use of the term "homopolymer" herein the reference is likewise to encompass impliedly a polymer in which there is not a significant amount of another component. Of course, most commercial grades of maleic anhydride may contain some quantity of other polymerizable compounds, and it would be possible (although not advisable) to add trivial amounts of another unsaturated compound. What is important is that the quantity of other components in the polymer be sufficiently low that the performance of the polymer is not significantly impaired. Generally, the polymer will be at least 90%, desirably at least 92%, more desirably at least 94%, preferably at least 96%, more preferably at least 98% and most preferably at least 99% composed of repeating units of maleic anhydride. Thus, while the term "homopolymer" is used herein for conciseness, the compositions and techniques should be recognized to be applicable to such limited copolymers as well.

The maleic anhydride is polymerized to yield a polymer having the general structure:

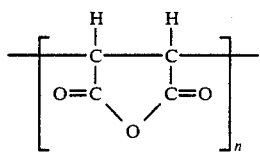

wherein n is greater than 2, desirably 2 to 100, more desirably 2 to 50, preferably 2 to 20, and most preferably 2 to 10. While the higher molecular weights (i.e., n =11 to 100, or more) would be operable, such polymers are very difficult to produce. The lower molecular weights (i.e., n=2 to 10) are preferred because of their relative ease of manufacture. The polymerization takes place by conventional means, preferably including a free radical catalyst. Suitable free radical catalysts include peroxides such as hydrogen peroxide, t-butyl peroxide, t-butyl hydroperoxide, and cumene hydroperoxide; persulfates such as sodium persulfate, potassium persulfate, and ammonium persulfate; and azo compounds such as azobisisobutronitrile. The peroxides, especially t-butyl peroxide, are preferred catalysts. Because the polymerization of maleic anhydride is a rather slow and "difficult" reaction, the amount of catalyst used will desirably be greater than in a typical polymerization. Generally, the catalyst will be present at 0.01 to 25, desirably 0.1 to 20, and preferably 1 to 15 weight percent, based on the weight of the monomer.

The polymerization reaction may take place at any suitable temperature, for instance at 50° C. to 250° C., preferably at 100° C. to 200° C. If no catalyst is used, the preferred polymerization temperature is 105° C. to 160° C.

If a catalyst is used, the polymer will usually be such that the molecular weight will correspond to n being from 5 to 7. If no catalyst is used (i.e., only heat is used to drive the polymerization) n will be from 2 to 4.

The polymerization preferably takes place in a solvent such as diethylene glycol dimethyl ether. The polymerization reaction will generally be complete in 1 to 20 hours, desirably 2 to 10 hours.

After the polymerization is complete, the maleic anhydride homopolymer will be reacted with an amine of the formula:

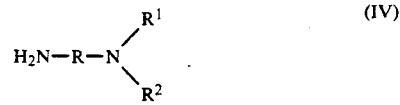

wherein R is an alkylene radical, preferably unbranched, having 1 to 12, desirably 2 to 8, preferably 2 to 6, more preferably 2 to 4, and most preferably, 3 carbon atoms; and $R^1$ and $R^2$ are each independently H or alkyl radicals having 1 to 12, desirably 1 to 8, more desirably 1 to 4, preferably to 3, more preferably or 2, and most preferably, 1 carbon atoms; with the proviso that at least one (preferably both) of $R^1$ and $R^2$ is alkyl. An exemplary amine is N,N-dimethyl-1,3-diaminopropane:

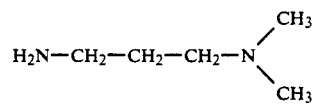

The polymaleic anhydride is reacted with the amine either with or without water. It is believed that an amide will be formed first, and heating will result in formation of the imide from the amide. The reaction of the polymer with the amine, with or without water, generally takes place in 0.1 to 2 hours at ambient temperature to 300° C., without a catalyst. At higher temperatures, e.g., 100° C. to 300° C., the byproduct water will be continually removed. The polymer and the amine will generally be reacted at a ratio of 0.9 to 1.1 mole of amine per mole of anhydride unit.

The structure of the polyimide will generally be:

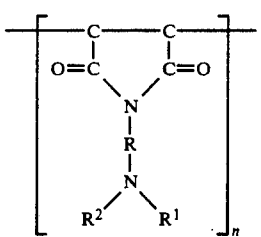

The amine polyimide is then quaternized by the addition of a quaternization agent such as an alkyl halide or a dialkyl sulfate. Exemplary quaternization agents include methyl bromide, ethyl bromide, methyl iodide, ethyl iodide, methyl chloride, and ethyl chloride. The degree of quaternization (i.e., the percent of the amino groups which become quaternized) is desirably at least 40%, more desirably at least 50%, preferably at least 60%, more preferably at least 70%, and most preferably at least 80% The quaternized polymer will have the general structure:

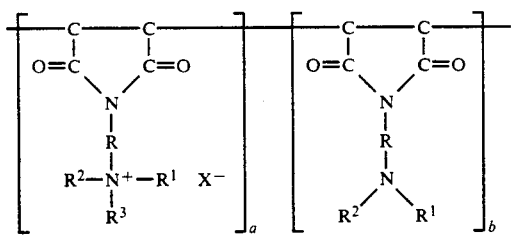

(VII)

in which a+b=n and $R^3$ is the moiety supplied by the quaternization agent. $R^3$ is an organic moiety desirably having 1 to 12 carbon atoms, more desirably an alkyl moiety having 1 to 12, more desirably 1 to 6, preferably 1 to 4, and more preferably or 2 carbon atoms. The quaternization is believed to occur randomly, and Structure VII is not necessarily intended to represent a polymer having discrete blocks of quaternized and non-quaternized units.

The quaternization (and the imide formation) can take place in the solvent used to form the original homopolymer.

The fluid containing the composition of the invention is then contacted with the clay to be stabilized in a conventional manner, such as by injecting the fluid under pressure into the well bore. The compositions of the invention are particularly suitable for use in water-based hydraulic fracturing fluids which are injected into oil wells under very high pressure to cause the rock of the oil formation to crack, leaving channels for the oil to flow to the well bore.

The invention will be further illustrated by the following examples. In the examples, all parts and percentages are by weight unless otherwise specified.

EXAMPLE 1

Step A 49.0 g of maleic anhydride and 42.2 g diglyme (diethylene glycol dimethyl ether) were combined in a 500 ml flask and heated to 120° C. 4.9 g of di-tertiarybutyl peroxide in 4.9 g of diglyme were added dropwise so as to not allow the exothermic reaction to raise the temperature over 155° C. As the reaction subsided, the mixture was maintained at 130° C. for five hours. Based on NMR analysis, it was estimated that 5% of the maleic anhydride was unreacted.

Step B

The solution of Step A (missing 0.5 g which was used for analysis) was combined with 50 g of water and heated to 90° C. 51 g of N,N-dimethyl-1,3-diaminopropane was added dropwise. A small amount of solid formed on the side of the reaction vessel, but was removed. An additional 100 g of water were then added.

Step C The solution of Step B was combined with 25.5 g of chloromethane and heated to 90° C. for five hours. The product was identified as the 57% quaternary ammonium salt of the N,N-dimethyl-1,3-diaminopropane imide of polymaleic anhydride:

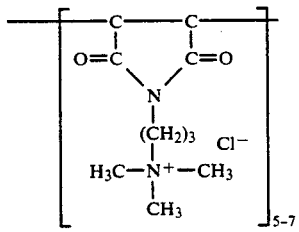

EXAMPLE 2

A 280 g portion of the compound of Example 1 was treated with an additional 5 g of chloromethane for five hours at 90° C. The resultant product was 83% quaternized.

EXAMPLE 3

(Comparative)

A 1 inch (25.4 mm) long, 1 inch (25.4 mm) diameter core of Berea sandstone (purchased from Cleveland Quarries of Amherst, Ohio) was soaked for 24 hours in an 8% NaCl solution, wrapped (around the circumference) with TEFLON®tape, inserted into a rubber sleeve, and placed in a core test cell. 25 ml of 8% NaCl solution was then forced axially through the core under a nitrogen gas pressure of 20 psi (138 kPa) and the time required for the saline to pass through the core recorded as 35 seconds. Two additional 25 ml portions of saline were passed through the core in a similar manner, those trials requiring 38 and 37 seconds. An attempt was then made to pass 25 ml of deionized water through the core in a similar manner, but after one minute only 2.9 ml of water had been collected and the flow of water stopped completely. This indicated that the deionized water caused the clay in the rock to swell.

EXAMPLE 4

In a manner similar to Example 3, a core was wrapped and placed in a core test cell. Three 25 ml portions of saline were forced through the core, followed by treatment with a 25 ml portion of a 0.1% (active) solution of the polymer of Example 1, forced through the core. Then three 25 ml portions of deionized water were forced through the core and the third flow rate for the water compared to the third flow rate for the saline, as a percentage of the latter, was calculated. The procedure was then repeated for several other treatments with various polymer concentrations and degrees of quaternization. The data are reported in Table I.

TABLE I

| Sample | Quat (%) | Concentration (%) | Fluid | Time (min:sec) | Flow (ml/s) | Return (%) |
|---|---|---|---|---|---|---|
| 1* | | | saline | 0:35 | | |
| | | | | 0:38 | | |
| | | | | 0:37 | 40.5 | |
| | no polymer | | | | | |

TABLE I-continued

| Sample | Quat (%) | Concentration (%) | Fluid | Time (min:sec) | Flow (ml/s) | Return (%) |
|---|---|---|---|---|---|---|
|   |   |   | water | ∞ | 0 | 0 |
| 2 |   |   | saline | 1:03 |   |   |
|   |   |   |   | 1:07 |   |   |
|   |   |   |   | 1:09 | 21.7 |   |
|   | 57 | 0.1 | treatment water | 2:11 |   |   |
|   |   |   |   | 2:34 |   |   |
|   |   |   |   | 3:01 |   |   |
|   |   |   |   | 3:13 | 7.8 | 35.9 |
| 3 |   |   | saline | 0:37 |   |   |
|   |   |   |   | 0:50 |   |   |
|   |   |   |   | 0:59 | 25.6 |   |
|   | 57 | 0.25 | treatment water | 0:52 |   |   |
|   |   |   |   | 1:07 |   |   |
|   |   |   |   | 1:10 |   |   |
|   |   |   |   | 1:12 | 20.4 | 79.7 |
| 4 |   |   | saline | 0:34 |   |   |
|   |   |   |   | 0:34 |   |   |
|   |   |   |   | 0:34 | 44.3 |   |
|   | 57 | 0.25 | treatment water | 0:31 |   |   |
|   |   |   |   | 0:28 |   |   |
|   |   |   |   | 0:29 |   |   |
|   |   |   |   | 0:30 | 50.0 | 112.9 |
| 5 |   |   | saline | 0:56 |   |   |
|   |   |   |   | 1:01 |   |   |
|   |   |   |   | 1:00 | 58.1 |   |
|   | 75 | 0.1 | treatment water | 0:58 |   |   |
|   |   |   |   | 0:57 |   |   |
|   |   |   |   | 1:04 |   |   |
|   |   |   |   | 1:04 | 23.4 | 9.38 |
| 6 |   |   | saline | 0:55 |   |   |
|   |   |   |   | 1:00 |   |   |
|   |   |   |   | 0:59 | 25.3 |   |
|   | 75 | 0.25 | treatment water | 0:51 |   |   |
|   |   |   |   | 0:48 |   |   |
|   |   |   |   | 0:50 |   |   |
|   |   |   |   | 0:51 | 29.4 | 116.2 |
| 7 |   |   | saline | 0:36 |   |   |
|   |   |   |   | 0:37 |   |   |
|   |   |   |   | 0:37 | 41.0 |   |
|   | 83 | 0.1 | treatment water | 0:47 |   |   |
|   |   |   |   | 0:45 |   |   |
|   |   |   |   | 0:50 |   |   |
|   |   |   |   | 0:50 | 29.9 | 72.9 |
| 8 |   |   | saline | 0:37 |   |   |
|   |   |   |   | 0:36 |   |   |
|   |   |   |   | 0:35 | 42.7 |   |
|   | 83 | 0.25 | treatment water | 0:30 |   |   |
|   |   |   |   | 0:31 |   |   |
|   |   |   |   | 0:31 |   |   |
|   |   |   |   | 0:31 | 48.7 | 114 |
| 9 |   |   | saline | 1:10 |   |   |
|   |   |   |   | 1:16 |   |   |
|   |   |   |   | 1:12 | 20.9 |   |
|   | 89 | 0.1 | treatment water | 1:07 |   |   |
|   |   |   |   | 1:00 |   |   |
|   |   |   |   | 1:01 |   |   |
|   |   |   |   | 1:02 | 24.3 | 116.3 |
| 10 |   |   | saline | 1:03 |   |   |
|   |   |   |   | 1:19 |   |   |
|   |   |   |   | 1:11 | 21.3 |   |
|   | 89 | 0.25 | treatment water | 0:59 |   |   |
|   |   |   |   | 0:55 |   |   |
|   |   |   |   | 0:56 |   |   |
|   |   |   |   | 0:58 | 26.0 | 122.1 |

*Not an example of the invention.

The data in Table I show that at a given level of quaternization, a higher concentration of polymer in the treatment fluid produces a better return rate (Sample 2 vs. 3 or 4, Sample 5 vs. 6, Sample 7 vs. 8, and Sample 9 vs. 10) and that at a given concentration of polymer in the treatment fluid, a higher level of quaternization generally produces a better return (Sample 2 vs. 5 vs. 7 vs. 9 and Samples 3 or 4 vs. 6 vs. 8 vs. 10). Table I also shows that for a given treatment level and degree of quaternization, cores with higher saline flow rates are easier to treat (i.e., they receive more benefit) than cores with low saline flow rates (Sample 4 vs. 3).

EXAMPLE 5

(Comparative)

A solution of 29.26 g (0.209 mole) of 1-decene, 20.5 g (0.209 mole) of maleic anhydride, and 101 g of a mixed aromatic solvent was heated to 130° C. and 1.1 g of di-t-butyl peroxide was added. The mixture was maintained at 130° C. for five hours. An increase in viscosity was noted and the solution was cooled to 90° C. and diluted with an additional 28.3 g of the mixed aromatic solvent. The solution was then heated to 90° C. and 21.3 g of N,N-dimethyl-1,3-diaminopropane was added dropwise over a 30 minute period. The resulting solution was heated to reflux and the water removed. The remaining product and 78 g of water were heated with 10.5 g of chloromethane to 90° C. for two hours. The mixture was cooled and allowed to separate into aqueous and nonaqueous layers. The aqueous layer, containing the product, was recovered. The product was identified as the full quaternary salt of the imide of a copolymer of maleic anhydride and 1-decene (See WO 88/04680, above).

This compound was evaluated as in Example 4 and the results are reported in Table II.

TABLE II

| Sample | Quat (%) | Concentration (%) | Fluid | Time (min:sec) | Flow (ml/s) | Return (%) |
|---|---|---|---|---|---|---|
| 11* |   |   | saline | 1:18 |   |   |
|   |   |   |   | 1:21 |   |   |
|   |   |   |   | 1:23 | 18.0 |   |
|   | 100[1] | 0.1 | treatment water | 1:50 |   |   |
|   |   |   |   | 1:55 |   |   |
|   |   |   |   | 1:56 |   |   |
|   |   |   |   | 1:57 | 12.8 | 71.0 |
| 12* |   |   | saline | 1:18 |   |   |
|   |   |   |   | 1:20 |   |   |
|   |   |   |   | 1:23 | 18.1 |   |
|   | 100[1] | 0.25 | treatment water | 1:30 |   |   |
|   |   |   |   | 1:29 |   |   |
|   |   |   |   | 1:29 |   |   |
|   |   |   |   | 1:29 | 17.0 | 93.4 |

*Not an example of the invention.
[1]100% of the maleic imide groups, which comprise only 50 mole % of the polymer.

The data in Table II show that the copolymer stabilizes the clay in the core.

EXAMPLE 6

If a treatment polymer causes "oil wetting" of the clay in the core, the flow rate of water will increase, but the flow rate of oil will decrease. To determine if the compounds of the invention cause oil wetting, the procedure of Example 4 was repeated, except that kerosene was used instead of deionized water for the final fluid. The results are shown in Table III.

EXAMPLE 7

(Comparative)

The oompound of Samples 11 and 12 (Example 5) was evaluated as in Example 6 and the results are reported in Table III (Sample 15).

TABLE III

| Sample | Quat (%) | Concentration (%) | Fluid | Time (min:sec) | Flow (ml/s) | Return (%) |
|---|---|---|---|---|---|---|
| 13* |   |   | saline | 0:34 |   |   |

TABLE III-continued

| Sample | Quat (%) | Concentration (%) | Fluid | Time (min:sec) | Flow (ml/s) | Return (%) |
|---|---|---|---|---|---|---|
| | no polymer | | kerosene | 0:33 | | |
| | | | | 0:33 | | |
| | | | | 1:07 | | |
| | | | | 0:57 | | |
| | | | | 0:54 | 27.7 | 61.1 |
| 14 | | | saline | 0:33 | | |
| | | | | 0:32 | | |
| | | | | 0:33 | 45.5 | |
| | 83 | 0.25 | treatment kerosene | 0:29 | | |
| | | | | 1:04 | | |
| | | | | 0:59 | | |
| | | | | 0:56 | 27.0 | 59.3 |
| 15* | | | saline | 0:51 | | |
| | | | | 0:53 | | |
| | | | | 0:55 | 27.3 | |
| | 100[1] | 0.25 | treatment kerosene | 0:52 | | |
| | | | | 3:20 | | |
| | | | | 2:54 | | |
| | | | | 2:44 | 9.1 | 33.5 |

*Not an example of the invention.
[1]100% of the maleic imide groups, which comprise only 50 mole % of the polymer.

The data in Table III show that compared to a control sample with no treatment (Sample 13), the compound of the invention (Sample 14) does not cause oil wetting, as shown by a rate of return almost identical to that of the control. However, the copolymer treatment (Sample 15) does cause oil wetting, as evidenced by its very low rate of return for kerosene. In an oil well, Sample 15 would cause low production rates even if the clay had been stabilized.

SAMPLE 8

Because many oil wells are sufficiently deep that they are constantly at elevated temperature (e.g., 250° F. [121° C.] or higher), it is important that the treatment compound be stable at such temperatures. To evaluate such stability, the compound of Samples 9 and 10 was heated to 250° F (121° C.) for 18 hours and then evaluated as in Example 4. The results are shown in Table IV (Sample 16).

EXAMPLE 9

A mixture of 38.4 g (0.39 mole) of maleic anhydride in 38.4 g of methyl carbitol was heated to 50° C. until the maleic anhydride dissolved. 39.96 g (0.39 mole) of N,N-dimethyl-1,3-diaminopropane was then added dropwise over two hours with the temperature of the solution maintained at 90° C. or less. The temperature was then raised to 120°-130° C. for one hour. 111.5 of the solution (with water of reaction still present) was mixed with 57 g of additional water and the mixture treated with chloromethane to quaternize the imide. 1 g of solid byproduct was removed by filtration and the final product was identified as the 90% quaternary salt of the imide of poly(n=2 to 3) maleic anhydride.

This material was heated and evaluated as in Example 8. The results appear in Table IV (Sample 17).

EXAMPLE 10
(Comparative)

A one liter flask was charged with 200 g of a low molecular weight polyacrylamide aqueous solution (37.6% active, 480 cps Brookfield viscosity) and 85.9 g of 37% formaldehyde. To this solution was added dropwise 112.5 g of 40% dimethylamine. There was an exotherm to 40° C. and the mixture was stirred for one hour after the amine addition was complete. 327 g of this product was charged to the reactor for quaternization. Methyl chloride (43.9 g total) was charged to the reactor in portions and the solution was heated to 35°-40° C. for six hours. The mixture was cooled to room temperature. The pH of the solution was 7.0 The total nitrogen was 6.67%, and the basic nitrogen was 0.23%. This product was identified as the 93% quaternized polymer of the general structure:

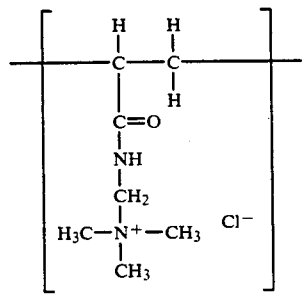

A 137.7 g sample of the above polymer was stabilized by the dropwise addition of 22.4 g of $H_2SO_3$ (final pH=4). This was designated Sample 18 and was evaluated as in Example 9.

A 66.7 g sample of the above polymer was stabilized by the addition of 7.9 g of acetic acid (final pH =5.5). This was designated Sample 19 and was evaluated as in Example 9.

TABLE IV

| Sample | Quat (%) | Concentration (%) | Fluid | Time (min:sec) | Flow (ml/s) | Return (%) |
|---|---|---|---|---|---|---|
| 16 | | | saline | 0:37 | | |
| | | | | 0:36 | | |
| | | | | 0:36 | 41.2 | |
| | 89 | 0.15 | treatment water | 1:16 | | |
| | | | | 1:29 | | |
| | | | | 1:19 | | |
| | | | | 1:01 | 24.3 | 59 |
| | | | | 0:46 | | |
| | | | | 0:42 | | |
| | | | | 0:41 | 36.3 | 88 |
| 17 | | | saline | 0:34 | | |
| | | | | 0:33 | | |
| | | | | 0:34 | 43 | |
| | 90 | 0.15 | treatment water | 1:53 | | |
| | | | | 1:26 | | |
| | | | | 1:07 | | |
| | | | | 0:51 | 29.1 | 66 |
| | | | | 0:40 | | |
| | | | | 0:39 | | |
| | | | | 0:38 | 38.7 | 88 |
| 18* | | | saline | 1:14 | | |
| | | | | 1:24 | | |
| | | | | 1:26 | | |
| | | 0.15 | treatment water | ∞ | | 0 |
| 19* | | | saline | 0:42 | | |
| | | | | 0:45 | | |
| | | | | 0:47 | 55.4 | |
| | | 0.15 | treatment water | 0:58 | | |
| | | | | ∞ | | 0 |

*Not an example of the invention.

The data in Table IV show that the polymers of the invention provide good return rates after sustained high temperature exposure, but the polyacrylamide material provides no clay stability after the same heating protocol (although that compound does provide clay stability if not heated).

What is claimed is:

1. A composition comprising a quaternary ammonium salt of an imide of a polymer of maleic anhydride selected from the group consisting of homopolymers of maleic anhydride and copolymers of maleic anhydride containing repeating units at least about 90% of which are maleic anhydride.

2. The composition of claim 1 having the general structure:

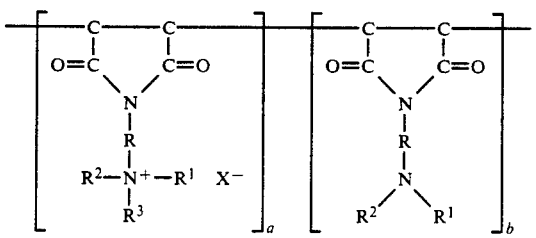

wherein a and b are integers, the sum of which is at least 2, $X^-$ is an anion, R is an alkylene radical having 1 to 12 carbon atoms, $R^1$ and $R^2$ are each independently H or alkyl radicals having 1 to 12 carbon atoms, and $R^3$ is an organic moiety.

3. The composition of claim 2 wherien $R^3$ has 1 to 12 carbon atoms.

4. The composition of claim 3 wherein $R^3$ is an alkyl moiety.

5. The composition of claim 4 wherein R has 2 to 6 carbon atoms.

6. The composition of claim 5 wherein R has 2 to 4 carbon atoms.

7. The composition of claim 6 wherein R has 3 carbon atoms.

8. The composition of claim 4 wherein at least one of $R^1$ and $R^2$ is alkyl.

9. The composition of claim 8 wherein both of R1 and $R^2$ are alkyl.

10. The composition of claim 9 wherein $R^1$, $R^2$, and $R^3$ have to 4 carbon atoms.

11. The composition of claim 10 wherein $R^1$, $R^2$, and $R^3$ have 1 to 2 carbon atoms.

12. The composition of claim 11 wherein $R^1$ and $R^2$ have 1 carbon atom.

13. The composition of claim 8 wherein $R^1$, and $R^2$ are H or have 1 to 4 carbon atoms and $R^3$ has 1 to 2 carbon atoms.

14. The composition of claim 13 wherein $R^1$ and $R^2$ are H or have 1 to 2 carbon atoms and $R^3$ has 1 to 2 carbon atoms.

15. The composition of claim 4 wherein $a+b=2$ to 100.

16. The composition of claim 15 wherein $a+b=2$ to 20.

17. The composition of claim 16 wherein $a+b=2$ to 10.

18. The composition of claim 4 wherein a is at least 40% of $a+b$.

19. The composition of claim 18 wherein a is at least 60% of $a+b$.

20. The composition of claim 19 wherein a is at least 80% of $a+b$.

21. The composition of claim 4 wherein the polymer contains less than 4% of repeating units other than maleic anhydride.

22. A method of stabilizing a clay-containing formation comprising contacting the formation with a composition comprising a quaternary ammonium salt of an imide of polymaleic anhydride.

* * * * *